United States Patent [19]
Borgione

[11] Patent Number: 4,749,551
[45] Date of Patent: Jun. 7, 1988

[54] HOLLOW-FIBER OXYGENATORS FOR BLOOD

[75] Inventor: Teresa Borgione, Piombino, Italy

[73] Assignee: Sorin Biomedica S.p.A., Saluggia, Italy

[21] Appl. No.: 910,411

[22] Filed: Sep. 22, 1986

[30] Foreign Application Priority Data

Sep. 24, 1985 [IT] Italy .................. 17407 A/85

[51] Int. Cl.$^4$ ............... A61M 1/14; B01D 13/00; C02F 1/44

[52] U.S. Cl. ........................ 422/48; 422/45; 128/DIG. 3; 210/323.2; 210/321.75; 210/321.84; 261/DIG. 28

[58] Field of Search ............... 422/45, 48, 231; 128/DIG. 3; 210/321.4, 433.2, 323.2; 261/DIG. 28

[56] References Cited

U.S. PATENT DOCUMENTS

| | | | |
|---|---|---|---|
| 3,552,934 | 1/1971 | Claydon et al. | 422/231 |
| 3,743,707 | 7/1973 | Iwase et al. | 422/231 |
| 3,769,162 | 10/1973 | Brumfield | 128/DIG. 3 |
| 4,048,072 | 9/1977 | McCullough | 261/122 |
| 4,179,380 | 12/1979 | Amicel et al. | 422/48 |
| 4,240,907 | 12/1980 | Bentley | 210/646 |
| 4,365,978 | 12/1982 | Scott | 261/122 |

FOREIGN PATENT DOCUMENTS 0046583 6/1981 European Pat. Off. .

Primary Examiner—Barry S. Richman
Assistant Examiner—Lynn M. Kummert
Attorney, Agent, or Firm—Hedman, Gibson, Costigan & Hoare

[57] ABSTRACT

In a hollow-fiber oxygenator consisting of a container containing a plurality of fibers joined into a bundle and open at their ends to allow the passage into them of a first fluid (blood) and over the outside of which flows a second fluid (oxygen-carrying gas) which diffuses between them, a diffuser for the second fluid is provided which consists of several arms disposed in an array and is introduced between the fibers in positions close to the terminal zone of the fibers themselves.

7 Claims, 3 Drawing Sheets

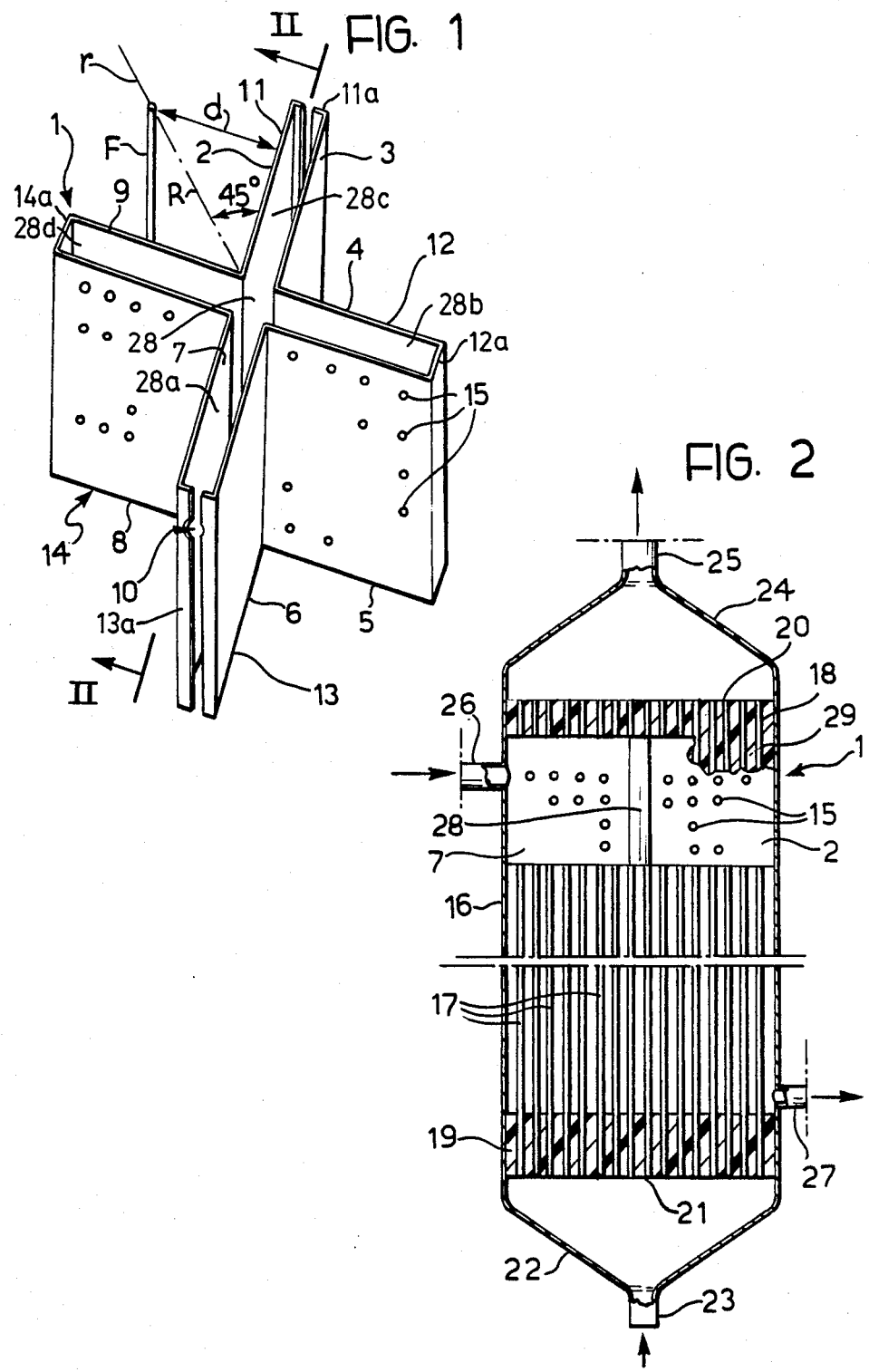

HOLLOW-FIBER OXYGENATORS FOR BLOOD

The present invention relates to oxygenators for blood of the type termed "hollow-fiber oxygenators" in the art, and particularly concerns improvements in these oxygenators so as to improve the gaseous exchange of oxygen and carbon dioxide in the blood.

It is known that, in cardiac surgery, it is necessary to institute extra-corporeal circulation of the blood during the operation so as to carry out artificially the physiological function of the lungs; in order to carry out this function a device—termed an oxygenator—has been devised which is able to achieve the removal of carbon dioxide from he venous blood of the patient and the simultaneous introduction of oxygen to convert it into arterial blood which returns to the patient. These oxygenators are normally used once and then thrown away.

One of the more important problems in the artificial oxygenation of blood is the capacity to remove sufficient carbon dioxide and to introduce an adequate quantity of oxygen without doing anything to the blood which would change its biochemical characteristics; in essence one is considering making the operation as close as possible to that of the human lung. In order to achieve this it is necessary for the greatest possible number of blood particles to come into intimate contact with the oxygen particles and to exchange their carbon dioxide content with them.

Various types of oxygenators have been proposed up to now and the most widely used of these are of two types: the "bubble" type in which the oxygen is introduced directly into the blood and gaseous exchange occurs during bubbling of the gas through liquid, and the "hollow fiber" type in which the exchange occurs through the semi-permeable wall of hollow fibers of suitable material. The second type seems to give a better guarantee from the point of view of conservation of the biochemical characteristics of the blood.

In the hollow-fiber oxygenator the blood is passed through numerous fibers (several tens of thousands) made from a polyolefin resin, for example polypropylene or polyethylene, having a diameter which can vary from 100 to 300 $\mu$m and extremely porous walls (from 20 to 80%) with a pore size such as to be permeable to gases but not to liquids; the gaseous exchange of the carbon dioxide in the blood flowing inside the walls and the oxygen flowing outside them occurs through these walls. Generally, these fibers are joined into a bundle which is sealingly inserted in a cylindrical container. The bundle has, however, a radial distribution of fibers which is not perfectly homogeneous: there is a greater density in the central part of the bundle and a lesser density in the peripheral zone. This means that it is difficult for the oxygen introduced into the container by a nozzle located, for example on its outer circumference to reach the central fibers, or at least the amount reaching them is very small, while there is preferential passage over those which can be reached most easily by the gas, that is the fibers closest to the nozzle, with a severe lowering of the specific average oxygenation rate of the blood treated.

Various devices have been proposed to remedy this disadvantage: some have been found to be inadequate; others are so complex as to be difficult and expensive to put into effect.

In avoidance of these disadvantages, the device of the present invention, which enables the total oxygenation of all the fibers in the bundle to be effected constantly and uniformly, is easy to realize and makes it possible to shorten the fibers suitably as a result of the increase in the oxygenation rate over the whole radius and the entire length of the fibers themselves, resulting in reductions in the treatment times, more manageable apparatus, and lower costs.

The main subject of the present invention is a hollow-fiber oxygenator constituted by a substantially cylindrical container; a collector for a first input fluid; a plurality of hollow fibers joined into a bundle in the container, the fibers being fixed at their end portions by a suitable adhesive and being open at their ends to allow the first fluid to enter them; a second collector for the first fluid leaving the fibers; inlet and outlet nozzles in the container for the first fluid; an inlet nozzle to the container for a second fluid which diffuses between the fibers, flowing over their outer surfaces; an outlet nozzle from the container for the second fluid, and a diffuser for the second fluid, which is constituted by several arms disposed in an array about an axis, the arms being constituted by substantially parallel, facing walls, each pair of adjacent walls belonging to two consecutive arms forming a dihedron, the end walls of which are substantially parallel to the axis, the diffuser being introduced between the fibers in a position close to the end portion of the fibers often to the second collector and in communication with the inlet nozzle for the second fluid.

These and other characteristics of the invention will become clearer from the following description of several preferred embodiments thereof, taken in conjunction with the appended drawings, in which:

FIG. 1 is a schematic view of a first embodiment of the diffuser of the present invention;

FIG. 2 is a schematic median longitudinal sectional view of the oxygenator in which the first embodiment of the diffuser of the present invention is used, taken on the line II—II of FIG. 1;

Figure 2A:
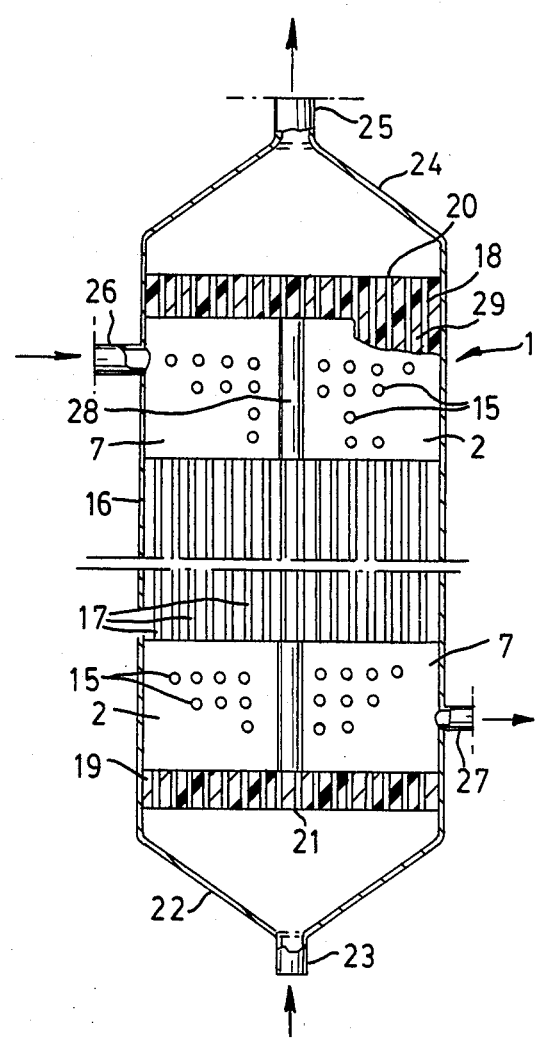
FIG. 2A is a schematic median longitudinal sectional view of the oxygenator of FIG. 2, illustrating the use of a pair of diffusers of the present invention, such as the diffuser of FIG. 1.

With reference to FIG. 1, the diffuser of the invention is indicated 1 and is constituted in the first embodiment by four diffuser elements (arms) 11, 12, 13, 14 which are disposed in a cross and each of which is formed by two substantially parallel walls; the walls 2 and 3 form the arm 11, the walls 4 and 5 form the arm 12, the walls 6 and 7 the arm 13, the walls 8 and 9 the arm 14. The adjacent walls of two consecutive arms (3, 4; 5, 6; 7, 8; 9, 2) form, in pairs, dihedrons with substantially parallel end walls 11a, 12a, 13a and 14a.

A hole or opening 10 for the immission of an oxygen-carrying gas is formed in an end wall, for example the end wall 13a.

A plurality of apertures 15 of dimensions such as to promote the passage of the oxygen therethrough is formed in each of the eight walls 2-9 of the diffuser.

The diagram of FIG. 2 shows the principle structure of hollow-fiber oxygenators well known in the art, in median longitudinal section. The structure is illustrated in outline so as to show the insertion therein of the diffuser of the present invention.

In it, a generally cylindrical container, indicated 16, houses a bundle 17 of hollow fibers of semi-permeable material with the dimensions given in the introduction to the present specification. Fibers having these characteristics are available commercially as is well known to experts in the art.

Two zones of fixing of the fibers are indicated 18 and 19, the fixing being achieved by the introduction of an adhesive resin (generally polyurethane) between the fibers and its subsequent setting. Fibers of the bundle 17 pass through the zones 18 and 19 and face the respective surfaces 20, 21 formed by the adhesive resin, presenting their hollow circular sections thereto.

A collector for a first fluid—in this embodiment blood—coming from a nozzle 23 is indicated 22; the blood will enter the bundle of fibers 17 through their ends which open at the surface 21.

A second collector, is indicated 24, is arranged to receive the blood leaving the ends of the bundle of fibers 17 which open at the surface 20, the blood flowing out of the oxygenator through a nozzle 25.

Oxygen is introduced through a nozzle 26 and diffuses between the fibers of the bundle 17 so as to replace the carbon dioxide in the blood during its passage between the fibers in counter-current to the blood which flows within the fibers, this exchange being possible because of the semi-permeable nature of the fibers themselves. The mixture of the remaining oxygen and the carbon dioxide removed finally leaves through a second nozzle 27.

In FIG. 2, the diffuser 1 of FIG. 1 is obviously shown in median section.

It is inserted into the upper part of the fibers of the bundle 17 close to their end portions. The walls 7 and 2 of the diffuser 1, the interior of which is left open by the median section along the line 2—2 of FIG. 1, can be seen in the drawing.

The central zone 28 is the opening or space between the radiating arms 11, 12, 13 and 14 and corresponds to the area formed by the connection between adjacent walls 3 and 4, 5 and 6, 7 and 8 and 9 and 2.

The upper part 29 (FIG. 2) of the diffuser is inserted in the zone 18 of fixing of the fibers and is thus also fixed in the bonding resin. It does not reach the end surface 20 formed by the bonding resin where the fibers open but remains embedded within the adhesive itself.

The operation of the oxygenator provided with the diffuser of the invention will now be described with reference to FIGS. 1 and 2.

The venous blood enters the nozzle 23, fills the collector 22, enters the bundle 17 of hollow fibers through their ends which are open at the surface 21, and then passes through them to their opposite ends facing the surface 20.

Simultaneously, a current of oxygen introduced by the nozzle 26 passes through the hole 10 of the diffuser 1 and into the space 28a between the walls 6 and 7 of the arm 13 and into the spaces 28b, 28c and 28d between the walls of the other arms 11, 12 and 14, and, diffuses through the apertures 15 present in the walls of the diffuser, and penetrates between the fibers of the bundle 17 to bathe them so completely as to be almost homogeneous. In fact, the gas pressure will not drop to such a level at any point in the bundle as to compromise its further advance, in that the path of the oxygen flow will always be much less than the radius of the bundle 2. In fact, the maximum path of the gas can be calculated from simple considerations of elementary geometry.

If the fiber F (FIG. 1) located in the most unfavourable position is considered, that is, on the radial plane r forming two dihedral angles of 45° with the walls 9 and 2, and at a distance R (equal to the inner radius of the container 16 of FIG. 2) from their common edge, the distance d from the said walls will be $R/\sqrt{2}$, that is about 0.7 R.

The diffuser 1 (FIG. 1) is made from any plastics material which can be molded into the desired form and perforated. For example, it could be a polycarbonate or styrene-acrylonitrile or the like.

The method of manufacture may consist, for example, of moulding two halves (wall 6, arm 12 and wall 3; wall 7, arm 14 and wall 2) which are mirror images because of the hole 10 which must be between the two facing halves. Methods of this type fall within the normal practice of moulded plastics technology.

The fixing of the diffuser 1 within the bundle of fibers 17 (FIG. 2) is carried out simultaneously with the fixing of the fibers, for example, by the introduction of the adhesive into the bundle in the fluid state, followed by centrifuging and setting. These are also methods which are well known to the expert in the art.

It is important to note that the insertion of the diffuser 1 into the bundle 17 does not cause disorder in the geometry of the fibers. In fact, the thickness of the arms is extremely small, in effect no greater than 2.5 mm, which is sufficient for the passage of the gas without a drop in pressure but far from creating alterations in the geometry of the bundle and preferential paths for the gas. The absence of changes in the geometry of the ordering of the fibers means that they come together at the end of the diffuser without twisting or stretching, and the absence of preferential paths for the gas achieves the specific function of the diffuser 1: to carry the oxygen without a pressure drop to all the fibers so that the bathing of the fibers in the last part of the gas path is practically homogeneous throughout the bundle.

A second embodiment of the invention provides for the supply of the oxygen to a central position of the oxygenator. In this case, the diffuser takes on the form shown schematically and indicated 30 in FIG. 3, in which the arms 31, 32, 33, 34 have an additional duct 35 which is parallel to them and to the edges of the dihedral components of the diffuser, and is located centrally relative to their spatial distribution.

Figure 3:
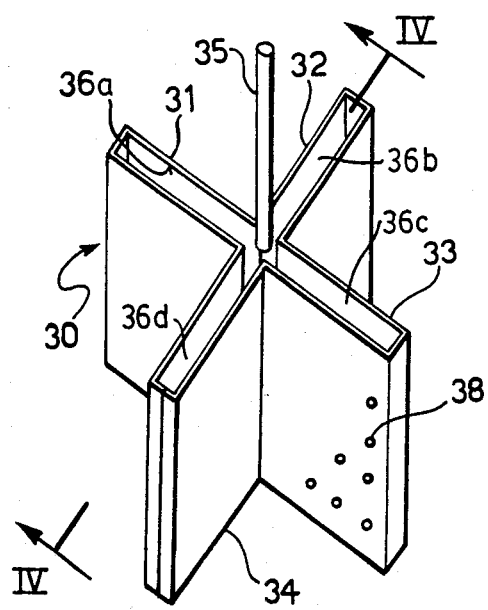
FIG. 3 is a schematic view of a second embodiment of the diffuser of the present invention.
Figure 4:
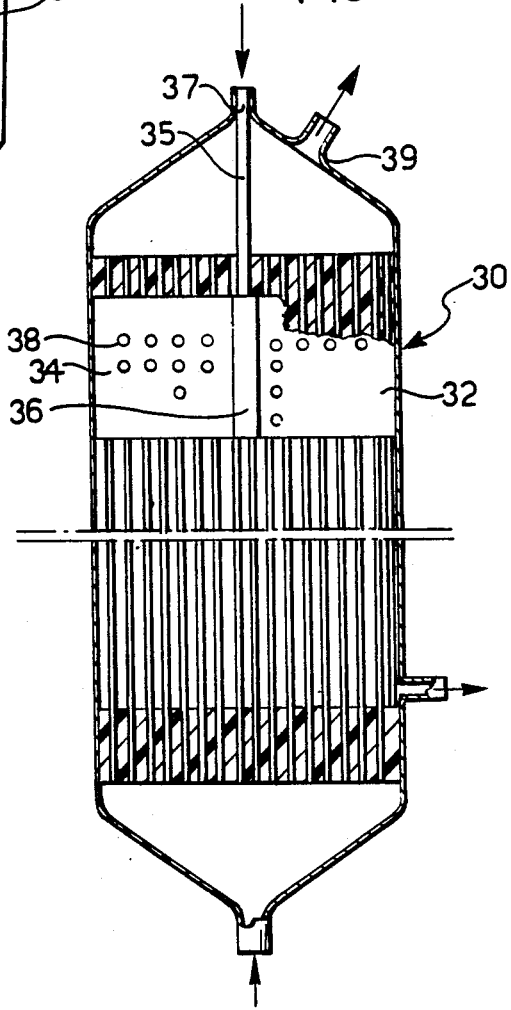
FIG. 4 is a schematic median longitudinal sectional view of the oxygenator in which the second embodiment of the diffuser of the present invention is used, taken on the line 4—4 of FIG. 3.

In FIG. 4, in which the general diagram of the oxygenator of FIG. 2 is repeated in median longitudinal section, the location of the diffuser 30 of FIG. 3 can be seen in a median section taken along the line 4—4. FIG. 4 also shows the oxygen supply duct 35, the arms 32 and 34 of which only one wall is of course shown, and the central zone 36 between the arms corresponding to the area of connection between the walls of the arms 31 32, 33 and 34 (FIG. 3). In this embodiment, the oxygen enters through the nozzle 37 (FIG. 4) and the duct 35, flows into the central channel 36 of the diffuser 30 into the cross-shaped spaces or zones 36a, 36b, 36c and 36d between the arms 31, 32, 33, 34 (FIG. 3) of the diffuser itself, and passes through the apertures 38 in its walls between the fibers in which the blood to be oxygenated flows.

The residual mixture of oxygen and carbon dioxide leaves the apparatus in the same way as shown in the embodiment of FIGS. 1 and 2. Clearly, the blood path will also be identical to the preceding example, with the sole difference that it will have to leave through the nozzle 39 located in a lateral position relative to the oxygen inlet 37.

The diffuser 30 is also made from plastics material and may be constructed by well-known moulding techniques. The duct 35 could be made in one piece with one half of the diffuser, for example the half including the arm 33.

Figure 5:
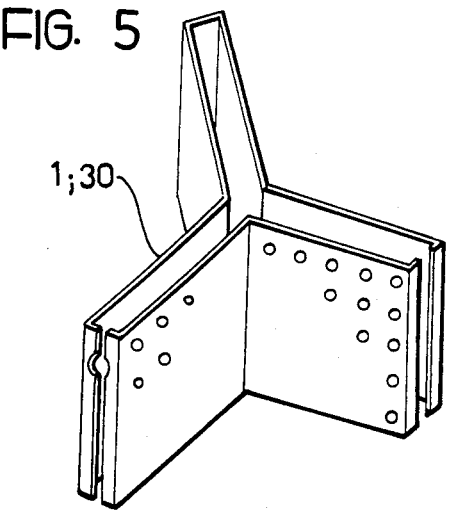
FIGS. 5, 6 and 7 are schematic views of other embodiments of the invention with different numbers of arms from those of the embodiments of FIGS. 1 and 3.
Figure 6:
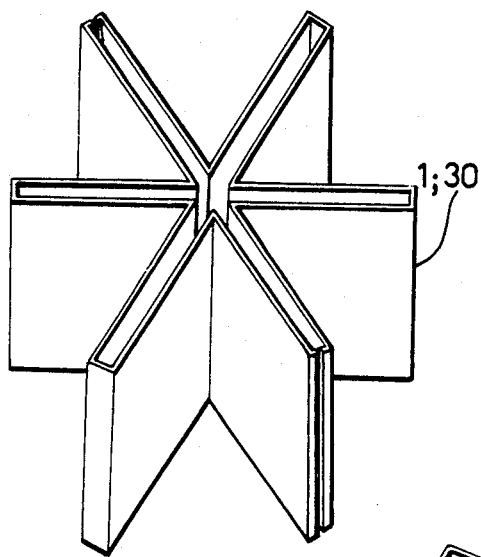
Figure 7:
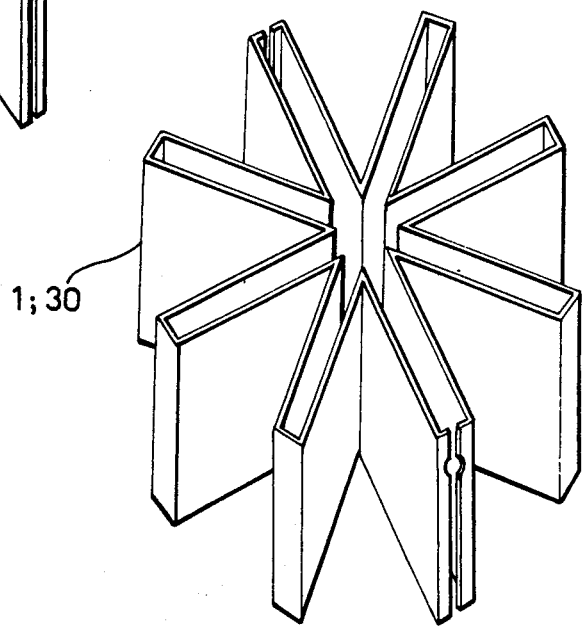

The diffuser, both in the embodiment of FIG. 1 and in that of FIG. 3, may have a different number of arms from four as long as this number is equal to or greater than two. FIGS. 5, 6 and 7 illustrate, by way of example, three-armed, six-armed, and eight-armed diffusers, respectively, in accordance with the first embodiment. If the number of arms is increased, the homogeneity of the oxygenation of the fibers is increased.

In all the illustrative embodiments, the walls have a plurality of apertures; the apertures could also be made in the areas of connection of the walls or only in these areas (e.g. areas forming or about the central spaces 28 and 36 of FIGS. 1 and 3), causing the gas to pass through the peripheral zone of the bundle of fibers, which could be sufficient, particularly if there were a very high number of arms.

For the oxygenator under consideration it is possible to envisage a structure which uses two diffusers, one located as described above and a second located close to the opposite end portion of the fibers and fixed in the zone 19 (FIG. 2A). In this case, it would act as a discharge and could be of the same type as the first, or of a different type with the same number of arms or a different number in the same angular positions or staggered by a certain angle, thus covering all possible combinations of the types given as examples.

Other modifications and variants could be made to the embodiments of the present invention, without thereby departing from the spirit of the invention.

I claim:

1. In a hollow-fiber oxygenator having a substantially cylindrical container, first and second opposing collectors within the container, a plurality of hollow fibers positioned within the container between said first and second collectors having semi-permeable walls and first and second end portions adhesively bonded together adjacent said first and second collectors, respectively and open thereto, an inlet in the container for conveying one fluid to be oxygenated into said first collector, through the hollow fibers for oxygenation and into said second collector, and an outlet in the container for conveying the one fluid which has been oxygenated from said second collector, the improvement comprising:
   a diffuser fixedly positioned between the fibers adjacent said first end portion thereof, including a plurality of arms in an array about an axis parallel to the longitudinal axis of the container, wherein each arm has a pair of substantially parallel facing walls having a space therebetween in communication with spaces between other pairs of facing walls of said arms and wherein each pair of adjacent walls of two consecutive arms form a dihedron therebetween, and apertures extending through the walls of said diffuser and in communication with spaces formed by said walls,
   an inlet in communication with said spaces in said diffuser for conveying a second oxygen containing fluid thereinto to be diffused through said apertures and over said semi-permeable fiber walls for the exchange of oxygen for a gas in the one fluid as the one fluid flows through fibers, and
   an outlet in the container for removing residual second fluid and gas.

2. An oxygenator as claimed in claim 1, wherein said facing walls are provided with apertures for the passage of the second fluid therethrough.

3. An oxygenator as claimed in claim 1, wherein said diffuser comprises more than two arms.

4. An oxygenator as claimed in claim 1, wherein said diffuser has means defining an opening for receiving the second fluid, the opening being formed in the central space between said walls of said arms, and said opening is in communication with the inlet for the second fluid.

5. An oxygenator as claimed in claim 1, wherein said plurality of arms of said diffuser extend radially across the substantially cylindrical container, and wherein said inlet for the second fluid includes a duct having an inner end extending axially into said diffuser and an outer end for receiving the second fluid to be conveyed into said diffuser.

6. An oxygenator as claimed in claim 1, wherein a second diffuser is provided adjacent to said second end portion of the fibers opposite to the first diffuser.

7. In a hollow fiber oxygenator for replacing carbon dioxide in blood with oxygen and having a substantially cylindrical container, first and second opposing collectors within the container at opposite ends thereof, a bundle of hollow fibers positioned within the container between said first and second collectors having semi-permeable walls and first and second end portions adhesively bonded together adjacent said first and second collectors, respectively and being open thereto, an inlet in said first end of the container for conveying blood to be oxygenated into said first collector, through the hollow fibers for oxygenation and into said second collector, and an outlet in said second end of the container for conveying oxygenated blood from said second collector, the improvement comprising:
   a diffuser adhesively bonded to and between the fibers adjacent the said second end portion of the fibers opening into said second collector, including a plurality of arms in an array about an axis parallel to the longitudinal axis of the container, wherein each arm has a pair of substantially parallel facing walls having a space therebetween in communication with spaces between other pairs of facing walls of said plurality of arms and wherein each pair of adjacent walls of two consecutive arms form a dihedron therebetween, and apertures extending through the walls of said diffuser and in communication with said spaces formed by said pairs of walls,
   an inlet in the container adjacent said second collector and in communication with said spaces in said diffuser for conveying oxygen thereinto adapted to diffuse through said apertures and over said semi-permeable walls to exchange oxygen for carbon dioxide in the blood as it flows through the fibers, and
   an outlet in the container adjacent to said first collector for removing residual oxygen and carbon dioxide.

* * * * *